US010646158B2

(12) United States Patent
Sakai

(10) Patent No.: US 10,646,158 B2
(45) Date of Patent: May 12, 2020

(54) METHOD OF USING AUTONOMIC NERVE FLUCTUATIONS AND SYSTEM USING THE SAME

(71) Applicant: Panasonic Intellectual Property Management Co., Ltd., Osaka (JP)

(72) Inventor: Masahiro Sakai, Kyoto (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 576 days.

(21) Appl. No.: 15/441,319

(22) Filed: Feb. 24, 2017

(65) Prior Publication Data
US 2017/0258396 A1     Sep. 14, 2017

(30) Foreign Application Priority Data

Mar. 10, 2016   (JP) ................................ 2016-047329

(51) Int. Cl.
| A61B 5/00 | (2006.01) |
| A61B 3/00 | (2006.01) |
| A61B 3/11 | (2006.01) |
| A61B 5/0245 | (2006.01) |

(52) U.S. Cl.
CPC ............ A61B 5/486 (2013.01); A61B 3/0091 (2013.01); A61B 3/112 (2013.01); A61B 5/0245 (2013.01); A61B 5/4035 (2013.01)

(58) Field of Classification Search
CPC ..... A61B 5/486; A61B 5/4035; A61B 3/0091; A61B 3/112; A61B 5/0245; A61B 5/0435
See application file for complete search history.

(56) References Cited

U.S. PATENT DOCUMENTS

2012/0277521 A1* 11/2012 Chamberlin .......... A61M 21/02
                                                                600/28
2014/0063461 A1*  3/2014 Yao ........................ A61B 3/113
                                                                351/210

FOREIGN PATENT DOCUMENTS

JP     2001-252265     9/2001
JP     2008-125802     6/2008

OTHER PUBLICATIONS

Masahito Sakakibara et al., "Heart rate variability biofeedback", Japanese Journal of Biofeedback Research, vol. 40, Issue 2, 43-46, 2013.

(Continued)

*Primary Examiner* — Eric F Winakur
*Assistant Examiner* — Abid A Mustansir
(74) *Attorney, Agent, or Firm* — Greenblum & Bernstein, P.L.C.

(57) ABSTRACT

A method includes: (a) obtaining information about a period of a fluctuation cycle in an autonomic nerve of a user at rest; (b) inducing the user to breaths in synchronization with the period of the fluctuation cycle in the autonomic nerve according to the obtained information; and (c) synchronizing a fluctuation in a diameter of a pupil of the user with the period of the fluctuation cycle in the autonomic nerve at the same time of (b) according to the obtained information. The period of the fluctuation cycle in the autonomic nerve is a period of a fluctuation cycle in the diameter of the pupil, a period of a fluctuation cycle in a heart beats of the user, or a period calculated from the period of the fluctuation cycle in the diameter of the pupil and the period of the fluctuation cycle in the heart beats.

11 Claims, 12 Drawing Sheets

(56) References Cited

OTHER PUBLICATIONS

Inger Ekman et al., "Voluntary Pupil Size Change as Control in Eyes Only Interaction", proceedings of the 2008 symposium on Eye tracking research & applications, 115-118, Mar. 26, 2008.

* cited by examiner

FIG. 2
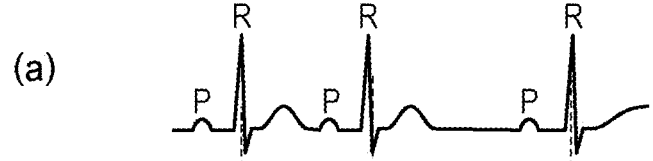
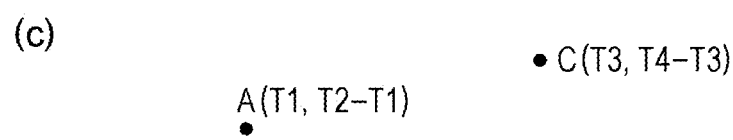
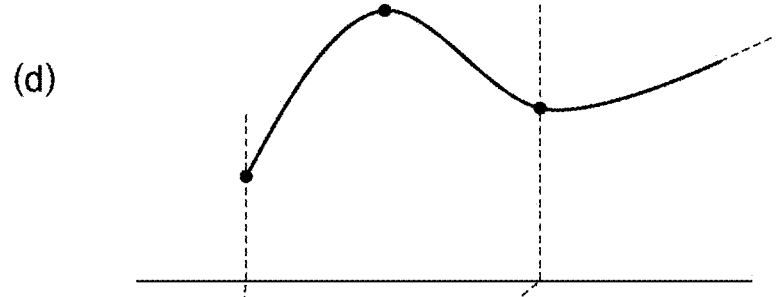

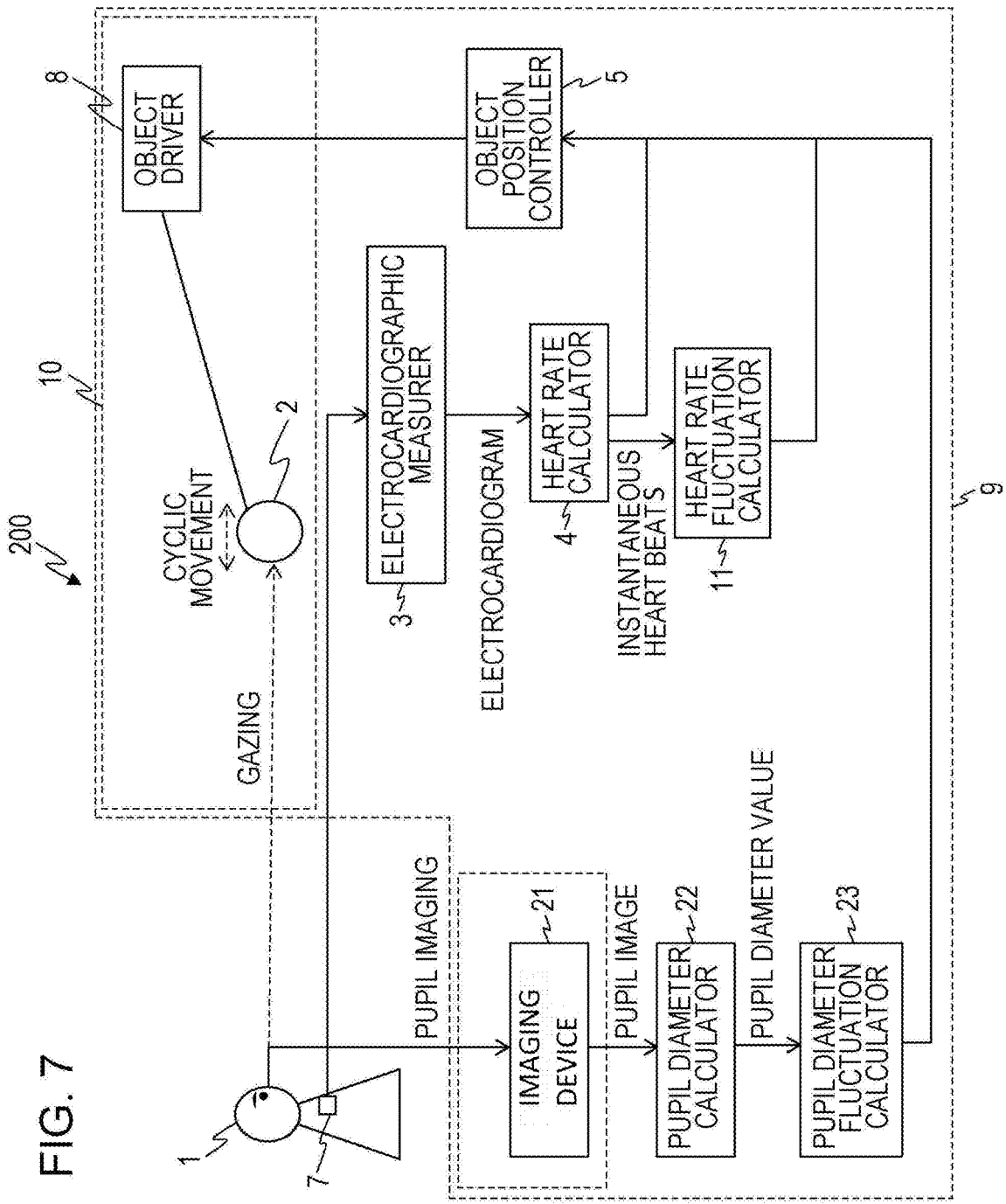

METHOD OF USING AUTONOMIC NERVE FLUCTUATIONS AND SYSTEM USING THE SAME

BACKGROUND

1. Technical Field

The present disclosure relates to a method of using autonomic nerve fluctuations and a system that uses these fluctuations.

2. Description of the Related Art

Biofeedback technology is under study in recent years. Biofeedback refers to technology or a phenomenon that enables the state in the body of a person to be consciously adjusted by feeding back information of which the person is not aware in an engineering way so that the person becomes aware of the information. For example, a stimulus that generates a physiological state homogeneous to a target physiological state of a test subject is applied to the test subject in consideration of the current heart rate, pulse rate, breathing rate, and other bio-information of the test subject. Therefore, the current physiological state of the test subject can be alleviated, and the test subject can be gradually induced to the target physiological state.

Conventional known biofeedback apparatuses are described in, for example, Japanese Unexamined Patent Application Publication Nos. 2008-125802 and 2001-252265.

Japanese Unexamined Patent Application Publication No. 2008-125802 discloses a technology by which biofeedback is performed by using a heart rate, myoelectricity, a blood pressure, a breathing rate, galvanic skin reflex, and the like. FIG. 11 illustrates a conventional biofeedback apparatus 600 described in Japanese Unexamined Patent Application Publication No. 2008-125802. A physiological measurer 63 in the biofeedback apparatus 600 obtains physiological information from a test subject (sometimes referred to as the user). The obtained information is sent to a state inferrer 64, which calculates an autonomic nerve activity index, after which the obtained information is transferred to a state determiner 65 and a control determiner 66 in that order. Finally, a stimulus presenter 68 presents some kind of stimulus to the user. In an embodiment in Japanese Unexamined Patent Application Publication No. 2008-125802, known heart rate variability biofeedback is used (see M. Sakakibara, P. Lehrer, "Heart rate variability biofeedback", Japanese Journal of Biofeedback Research, Vol. 40, Issue 2, 43-46 (2013), for example).

Japanese Unexamined Patent Application Publication No. 2001-252265 discloses a technology by which biofeedback is performed by using brain waves (or magnetoencephalography), biochemical reactions, a wink frequency, a skin resistance, sweating, voice intonation, body motion, mouse motion, dryness, head motion, a pupil size, facial expressions, a heart rate, a pulse rate, a breathing rate, a breathing state, and a body surface temperature. In Japanese Unexamined Patent Application Publication No. 2001-252265, the metal activity of the user is inferred by using the above information, and stimuli with intensities that are changed with time are applied to the five senses of the user by using a 1/f fluctuation theory or the like. FIG. 12 illustrates a conventional biofeedback apparatus described in Japanese Unexamined Patent Application Publication No. 2001-252265. A mental activity detector 71 detects various biological reactions of the user. A mental activity determiner 76 comprehensively analyzes the detection results. As a result, the mental activity state of the user is determined. A stimulus generator 73 applies stimuli having a time-varying intensity to the five senses of the user so as to attain the mental activity selected by a mental activity selector 74 as a target.

SUMMARY

One non-limiting and exemplary embodiment provides a method of using autonomic nerve fluctuations in a simple manner.

In one general aspect, the techniques disclosed here feature a method that includes: (a) obtaining information about a period of a fluctuation cycle in an autonomic nerve of a user at rest; (b) inducing the user to breaths in synchronization with the period of the fluctuation cycle in the autonomic nerve according to the obtained information; and (c) synchronizing a fluctuation in a diameter of a pupil of the user with the period of the fluctuation cycle in the autonomic nerve at the same time of (b) according to the obtained information. The period of the fluctuation cycle in the autonomic nerve is a period of a fluctuation cycle in the diameter of the pupil, a period of a fluctuation cycle in heart beats of the user, or a period calculated from the period of the fluctuation cycle in the diameter of the pupil and the period of the fluctuation cycle in the heart beats.(b)

In the method in one exemplary embodiment in the present disclosure, autonomic nerve fluctuations can be used in a simple manner.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 2 conceptually illustrates a procedure for converting an electrocardiographic signal output from an electrocardiographic measurer to instantaneous heart beats;

FIG. 7 schematically illustrates the structure of a biofeedback system in a second embodiment;

DETAILED DESCRIPTION

Figure 1:
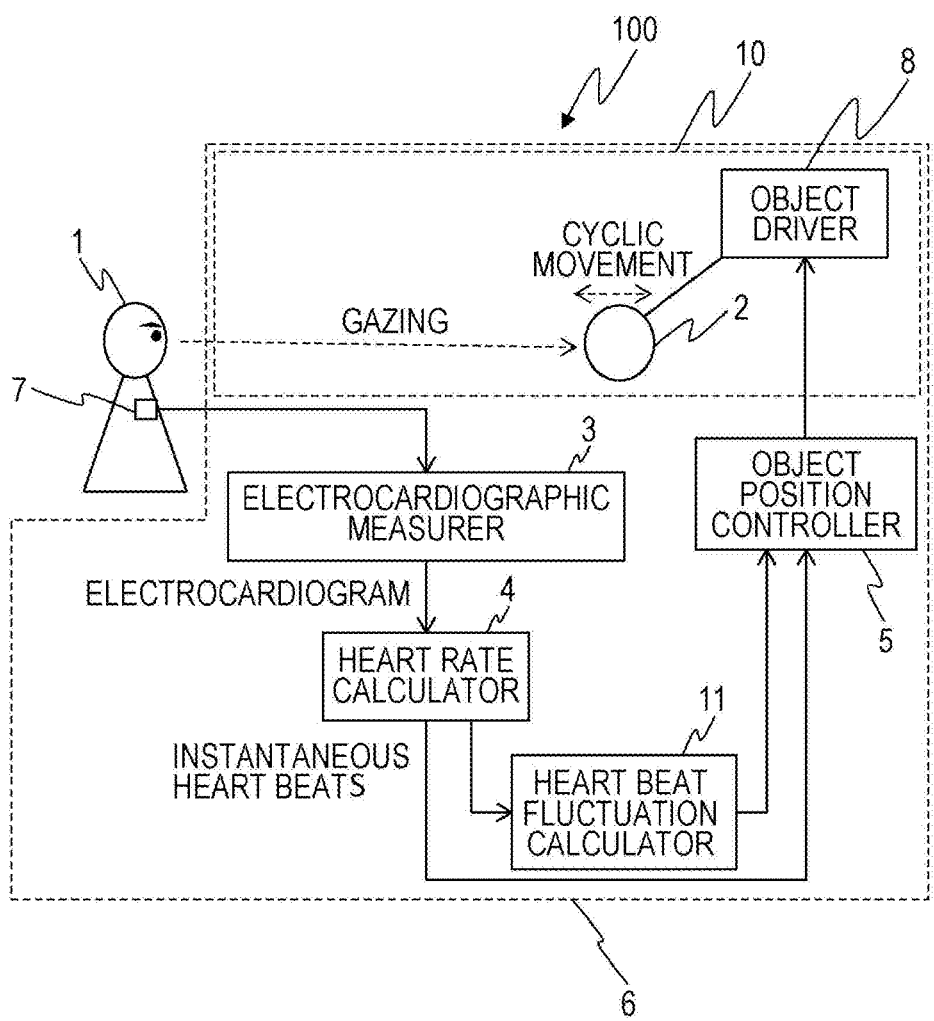
FIG. 1 schematically illustrates the structure of a biofeedback system in a first embodiment.

Findings on which the present disclosure is based will be described first.

In biofeedback technology, the physiological state of a person is controlled by feeding back information of which a person is not aware in an engineering way so that the person becomes aware of the information. In Japanese Unexamined Patent Application Publication No. 2008-125802, virtually only heart beats are specifically described as physiological information. The technology described therein is the same as the technology described in "Heart rate variability biofeedback" referred to above, the technology being related to heart rate variability biofeedback. In heart rate variability biofeedback, heart beats are controlled by slow diaphragmatic breathing. A study by the present inventor indicates that some users are not good at consciously performing slow diaphragmatic breathing. Even if a user can perform slow diaphragmatic breathing in a normal state, the user may not easily perform slow diaphragmatic breathing when, for example, the user is under strong stress. That is, there is case in which it is effectively difficult to perform heart rate variability biofeedback.

Although Japanese Unexamined Patent Application Publication No. 2001-252265 includes many descriptions of physiological information, they are generally known and specific embodiments are not included. In addition, although Japanese Unexamined Patent Application Publication No. 2001-252265 mainly proposes blinking of light having 1/f fluctuations and sounds as a feedback method, whether effects of feedback are exerted on obtained physiological information is neither verified nor confirmed; this is a matter of speculation.

After a diligent study, the present inventor came to the conclusion that when autonomic nerves are controlled by using both heart beat fluctuations and pupil diameter fluctuations instead of using only heart beat fluctuations, biofeedback is achieved more easily and more effectively.

As described above, in general biofeedback, a desired physiological state is induced by applying stimuli to a user to change the user's autonomic nerves. The autonomic nerves are composed of two nerves, sympathetic nerve and parasympathetic nerve. Since the sympathetic nerve and parasympathetic nerve complementarily work, the functions of organs and regions are automatically adjusted, regardless of the intention of the user. This is called double domination by the autonomic nerves. Unbalance between the sympathetic nerve and the parasympathetic nerve leads to a disease.

In heart rate variability biofeedback, which is typical biofeedback, heart beats are accessed through diaphragmatic breathing to adjust the autonomic nerves. Specifically, the user is made to intentionally breathe slowly so that variations in breathing are synchronized with periodic variations in blood pressure to achieve the maximum fluctuation in heart beats. Periodic variations in blood pressure (that is, periodic variations in a baroceptor at an end) form a low-frequency component in heart beat fluctuations; periodic variations in blood pressure are generally 0.04 to 0.15 Hz. Variations in breathing form a high-frequency component in heart beat fluctuations; variations in breathing are generally 0.15 to 0.50 Hz.

The present inventor noticed that, in heart rate variability biofeedback in which only abdominal breathing is used, if abdominal breathing is not possible, no effect is obtained from biofeedback and there is a case in which only a limited effect is obtained due to a factor other than diaphragmatic breathing such as stress. In view of this, the present inventor made a study of method by which an effect is obtained more reliably.

First, the present inventor pursued a study to see whether the pupil diameter can be intentionally changed by a convergence reaction caused by simple training. As a result, it was found that it is possible to intentionally cause changes in the pupil diameter due to convergence reflection. That is, it was clarified that when the user is made to gaze at a predetermined object in a relaxed manner, changes in the pupil diameter due to a convergence reaction can be induced by changing the distance between the object and the user. Since the pupil diameter is subject to double domination by the autonomic nerves, periodic variations in the pupil diameter are expected to be fed back to the autonomic nerves in the brain. As a result, it becomes possible to control the balance of the autonomic nerves.

In a further study by the present inventor, it was found that to cause the user to synchronize diaphragmatic breathing with the position of a moving object is easier than to command the user to simply perform diaphragmatic breathing or prompt the user to simply perform diaphragmatic breathing in synchronization with numerals, graphs, images, or the like.

Therefore, the present inventor performed biofeedback in which heart beat fluctuations and pupil diameter fluctuations are synchronized with each other, instead of performing heart beat fluctuations only by diaphragmatic breathing. Since heart beat fluctuations and pupil diameter fluctuations, which are both subject to domination by the autonomic nerves, are synchronized with each other unlike conventional heart rate variability biofeedback, a high biofeedback effect is practically obtained. In a method that uses biofeedback in which heart beat fluctuations and pupil diameter fluctuations are synchronized with each other, the present inventor confirmed that a higher effect is obtained when the degree of arousal of the test subject is high than when the degree is low.

As described above, the present inventor developed a biofeedback technology that is easier, simpler, more practical, and more effective than when conventional heart rate variability biofeedback methods are used.

One aspect of the present disclosure will be outlined below.

A method in one aspect of the present disclosure includes (a) obtaining information about a period of a fluctuation cycle in an autonomic nerve of a user at rest; (b) inducing the user to breaths in synchronization with the period of the fluctuation cycle in the autonomic nerve according to the obtained information; and (c) synchronizing a fluctuation in a diameter of a pupil of the user with the period of the fluctuation cycle in the autonomic nerve at the same time of (b) according to the obtained information. The period of the fluctuation cycle in the autonomic nerve is a period of a fluctuation cycle in the diameter of the pupil, a period of a fluctuation cycle in heart beats of the user, or a period calculated from the period of the fluctuation cycle in the diameter of the pupil and the period of the fluctuation cycle in the heart beats.

In step (c), the fluctuation of the diameter of the pupil of the user is synchronized with the period of the fluctuation cycle in the autonomic nerve by repeating, in the period of the fluctuation cycle in the autonomic nerve, a process that includes inducing a point of gaze of the user to move in a direction away from the user and inducing the point of gaze of the user to move in a direction to approach the user.

The period of the fluctuation cycle in the autonomic nerves may be a period corresponding to a peak frequency in a predetermined frequency band included in fluctuations in heat beats of the user at rest.

The predetermined frequency band may be from 0.04 to 0.15 Hz.

In step (c), if a heart rate is higher than an average heart rate at rest, the point of gaze of the user may be induced to move in a direction to approach the user. Note that "average" in this disclosure includes arithmetic mean.

In step (b), when the point of gaze of the user is induced to move in a direction away from the user in step (c), the user may be induced to inhale.

In step (c), the repeating of the process may include step (c1) of adjusting the point of gaze to an object by having the user gaze at the object and step (c2) of alternately repeating, after step (c1), motion of the object in a direction away from the user and motion of the object in a direction to approach the user.

In step (c), the repeating of the process may include step (c1) of displaying a three-dimensional image of an object on the screen of a display device, step (c2) of adjusting the point of gaze to the object by having the user gaze at the object, and step (c3) of alternately repeating, after step (c2) above, virtual motion of the object in a direction away from the user and virtual motion of the object in a direction to approach the user by changing the size of the object.

In step (c), the repeating of the process may include step (c1) of adjusting the point of gaze to a position illuminated by light by having the user gaze at the position illuminated by the light and step (c2) of alternately repeating, after step (c1), movement of the position illuminated by the light in a direction away from the user and movement of the position illuminated by the light in a direction to approach the user.

Information about the period of the fluctuation cycle in heart beats may be obtained from an electrocardiogram obtained in a measurement.

Information about the period of the fluctuation cycle in heart beats may be obtained by measuring a pulse wave.

A system in one aspect of the present disclosure includes: a storage device that holds information about the period of the fluctuation cycle in the autonomic nerves of a user at rest; and a processor that creates a control signal according to the information held in the storage device, the control signal being used to move an object according to the information held in the storage device, the processor synchronizing breathing of the user with the period of the fluctuation cycle in the autonomic nerves by moving the object in the period of the fluctuation cycle in the autonomic nerves in response to the control signal, the processor synchronizing fluctuations in the diameter of a pupil of the user with the period of the fluctuation cycle in the autonomic nerves.

A system in another aspect of the present disclosure includes: a storage device that holds information about the period of the fluctuation cycle in the autonomic nerves of a user at rest; and a controller that repeats a process that includes inducing a point of gaze of the user to move in a direction away from the user and inducing the point of gaze of the user to move in a direction to approach the user in the period of the fluctuation cycle in the autonomic nerves by moving an object in response to a control signal based on the information held in the storage device, the controller synchronizing breathing of the user with the period of the fluctuation cycle in the autonomic nerves.

Embodiments of the biofeedback apparatus in the present disclosure will be described with reference to the attached drawings.

First Embodiment

FIG. 1 schematically illustrates the structure of a biofeedback system 100 in this embodiment. For easy understanding, a user 1 is also illustrated.

The biofeedback system 100 will be outlined first.

In the biofeedback system 100, biofeedback is performed in which heart beat fluctuations, in which breathing of the user 1 is used, and pupil diameter fluctuations are synchronized with each other.

In the biofeedback system 100, information about the period of the fluctuation cycle in the autonomic nerves of the user 1 is obtained in advance while the user 1 is at rest. After that, the biofeedback system 100 concurrently performs two pieces of processing, (1) processing to synchronize breathing of the user 1 with the period of the fluctuation cycle in the autonomic nerves of the user 1 and (2) processing to synchronize fluctuations in the diameter of a pupil of the user 1 with the period of the fluctuation cycle in the autonomic nerves of the user 1. Processing in (2) may be implemented by inducing the point of gaze of the user 1 from a near position to a far position and from a far position to a near position.

In processing in (1), an idea in conventional heart rate variability biofeedback is used. When breathing of the user 1 is synchronized with the period of the fluctuation cycle in the autonomic nerves, it is possible to control heart beats. As a result, it becomes possible to adjust the autonomic nerve. Breathing is, for example, diaphragmatic breathing.

In processing in (2), the user 1 is commanded to gaze at an object 2. In this case, the biofeedback system 100 moves the object 2 toward and away from the user 1 in the above period of autonomic nerve fluctuations rather than an arbitrary period. The point of gaze of the user 1 gazing at the object 2 is induced from a near position to a far position and from a far position to a near position in the period of the fluctuation cycle in the autonomic nerves at rest. When the point of gaze moves, a convergence reaction is caused, changing the pupil diameter. As a result, it becomes possible to control the period of the autonomic nerves by using the period of the motion of the object 2 to change the pupil diameter dominated by the autonomic nerves.

The period of the motion of the object 2, the period being used in processing in (2), can be also used as a reference according to which the user 1 breathes in processing in (1). For example, the user 1 is commanded to inhale while the object 2 moves away from the user 1 and to exhale slowly in another term. As described in the findings by the present inventor, to cause the user 1 to synchronize diaphragmatic breathing with the position of the object 2 is easier than to cause the user 1 to simply perform diaphragmatic breathing.

In the processing described above, since synchronization is established between heart beat fluctuations and pupil diameter fluctuations, the period of autonomic nerve fluctuations can be more reliably led to the period of the fluctuation cycle in the autonomic nerves at rest. Furthermore, when the timing of the motion of the object 2 and the timing of breathing are related, diaphragmatic breathing can be easily induced. Therefore, biofeedback in the present inventor is more practical than the conventional biofeedback.

The structure of the biofeedback system 100, which performs the above processing, will be specifically described below.

The biofeedback system 100 includes a controller 6, an electrocardiographic sensor 7, and a feedbacker 10. The controller 6 includes an electrocardiographic measurer 3, a heart rate calculator 4, an object position controller 5, and a heart beat fluctuation calculator 11. The feedbacker 10 includes the object 2 and an object driver 8. These constituent elements will be described below in an order related to processing.

In the biofeedback system 100, the heart rate of the user 1 at rest is obtained before a biofeedback operation is performed. For this purpose, the electrocardiographic sensor 7, electrocardiographic measurer 3, heart rate calculator 4, and heart beat fluctuation calculator 11 are used, for example.

The electrocardiographic sensor 7, which is worn on the user 1, obtains an electrocardiogram of the user 1. Electrocardiographic data is output to the electrocardiographic measurer 3 in a wireless or wired manner.

The electrocardiographic measurer 3 receives the electrocardiographic data concerning the user 1 in a wireless or wired manner, converts the data to a form matching subsequent processing, and output the converted data to the heart rate calculator 4 as a electrocardiographic signal.

The heart rate calculator 4 receives the electrocardiographic signal and converts it to a signal that indicates instantaneous heart beats (instantaneous heart beat signal) by a conversion procedure described below. The instantaneous heart beats indicates a continuous signal obtained by converting the peaks of a plurality of R waves represented by voltage values to a form in which times (in seconds) are used, each of which represents an interval between the peaks of each two adjacent R waves, and smoothly linking these times these times by interpolation.

FIGS. 2(*a*) to 2(*e*) conceptually illustrate a procedure for converting an electrocardiographic signal output from the electrocardiographic measurer 3 to instantaneous heart beats.

FIG. 2(*a*) illustrates an example of the waveform of an electrocardiographic signal. The heart rate calculator 4 receives this waveform and performs processing described below on the waveform.

The heart rate calculator 4 first identifies the peaks of R waves of the electrocardiographic signal. For example, the heart rate calculator 4 identifies, as the peak of an R wave, a value that is equal to or larger than a predetermined threshold and takes a maximum value (peak). FIG. 2(*b*) illustrates the identified peaks of R waves together with times at which the peaks were identified.

The heart rate calculator 4 then converts the obtained data to an RR tachogram, that is, converts the value of the peak of each R wave indicated on the vertical axis to an RR time interval. Specifically, the heart rate calculator 4 replaces the value of peak A of the R wave obtained at time T1 with (T2−T1), T2 being a time at which a next peak was identified. As a result, peak A is converted to coordinates (T1, T2−T1). Similarly, the value of peak B of a second R wave obtained at time T2 is replaced with coordinates (T2, T3−T2). The value of peak C that follows is replaced with coordinates (T3, T4−T3).

FIG. 2(*c*) illustrates coordinates corresponding to the peaks obtained in processing described above.

The heart rate calculator 4 smoothly interpolates the discrete coordinates obtained as described above to obtain a curve. FIG. 2(*d*) illustrates a curve obtained by performing spline interpolation on the coordinates in FIG. 2(*c*). A technology for spline interpolation is known, so its detailed description will be omitted. Interpolation processing other than spline interpolation may be used. FIG. 2(*e*) illustrates a curve obtained from the peaks of R waves taken over a longer time. Each curve obtained in this way is instantaneous heart beats. In this embodiment, a time-averaged instantaneous heart beats is used as the heart beats of the user 1.

As is clear from the processing described above, the period of processing performed by the heart rate calculator 4 needs to be shorter than the RR time interval of the instantaneous heart beats.

Referring again to FIG. 1, the heart rate calculator 4 outputs the converted instantaneous heart beats to the heart beat fluctuation calculator 11. The heart beat fluctuation calculator 11 obtains information indicating the instantaneous heart beats.

The heart beat fluctuation calculator 11 obtains heart beat fluctuations from the waveform of instantaneous heart beats. For example, the heart beat fluctuation calculator 11 analyzes fluctuations in the frequency of the waveform of instantaneous heart beats. Specifically, the heart beat fluctuation calculator 11 calculates a power spectrum by a fast Fourier transform. In the fast Fourier transform, the present inventor used time-series information about pupil diameter values obtained over 50 seconds, as an example. The heart beat fluctuation calculator 11 uses the obtained fluctuations in the frequency of the waveform of the instantaneous heart beat to detect a peak frequency in a low-frequency (LF) region. Then, the heart beat fluctuation calculator 11 can obtain heart beat fluctuations. After that, the biofeedback system 100 performs a biofeedback operation. As described above, the heart beat fluctuation calculator 11 has obtained a period equivalent to the peak frequency of the LF component of heart beat fluctuations. This period can be said to be the period of the fluctuation cycle in the autonomic nerves of the user 1 at rest.

For a biofeedback operation to be performed, the heart beat fluctuation calculator 11 sends information about the period described above to the object position controller 5. The object position controller 5 creates a control signal by using information about instantaneous heart beats obtained in a biofeedback operation, the information being obtained later, and information about the period described above. The object driver 8 in the feedbacker 10 receives the control signal from the object position controller 5 and moves the object 2 so as to be synchronized with the period to prompt the user 1 to breaths. Thereby, it becomes possible to adjust the autonomic nerves in terms of both the pupil diameter and heart beats.

In the biofeedback operation, the electrocardiographic sensor 7 obtains the current electrocardiogram of the user 1. Subsequent processing remains the same until the heart rate calculator 4 outputs instantaneous heart beats.

The heart rate calculator 4 sends information about the instantaneous heart beats to the object position controller 5.

The object position controller 5 creates a control signal used to cause the object 2 to cyclically move from the instantaneous heart beats and the period of the fluctuation cycle in the autonomic nerves of the user 1 at rest, the period having been obtained in advance, by a method described below.

The object position controller 5 averages the instantaneous heart beats within a term equal to half a prescribed feedback period. The prescribed feedback period is the period of the fluctuation cycle in the autonomic nerves at rest. The object position controller 5 controls the object 2 differently depending on which is larger, the average instantaneous heart rate, HRave, that is inverse of mean of instantaneous heart beats or the average heart rate at rest, HRconst, that is inverse of mean of instantaneous heart beats at rest.

For example, if the HRave is larger than the HRconst, the object position controller 5 creates a control signal that controls the motion of the object 2 so that it moves toward the user 1. By contrast, if the H Rave is smaller than the HRconst, the object position controller 5 creates a control signal that controls the motion of the object 2 so that it moves away from the user 1.

Furthermore, in this embodiment, breathing is also involved in the user 1. For example, the user 1 is commanded to inhale while the object 2 moves away from the user 1 and to exhale slowly in another term.

Figure 3:
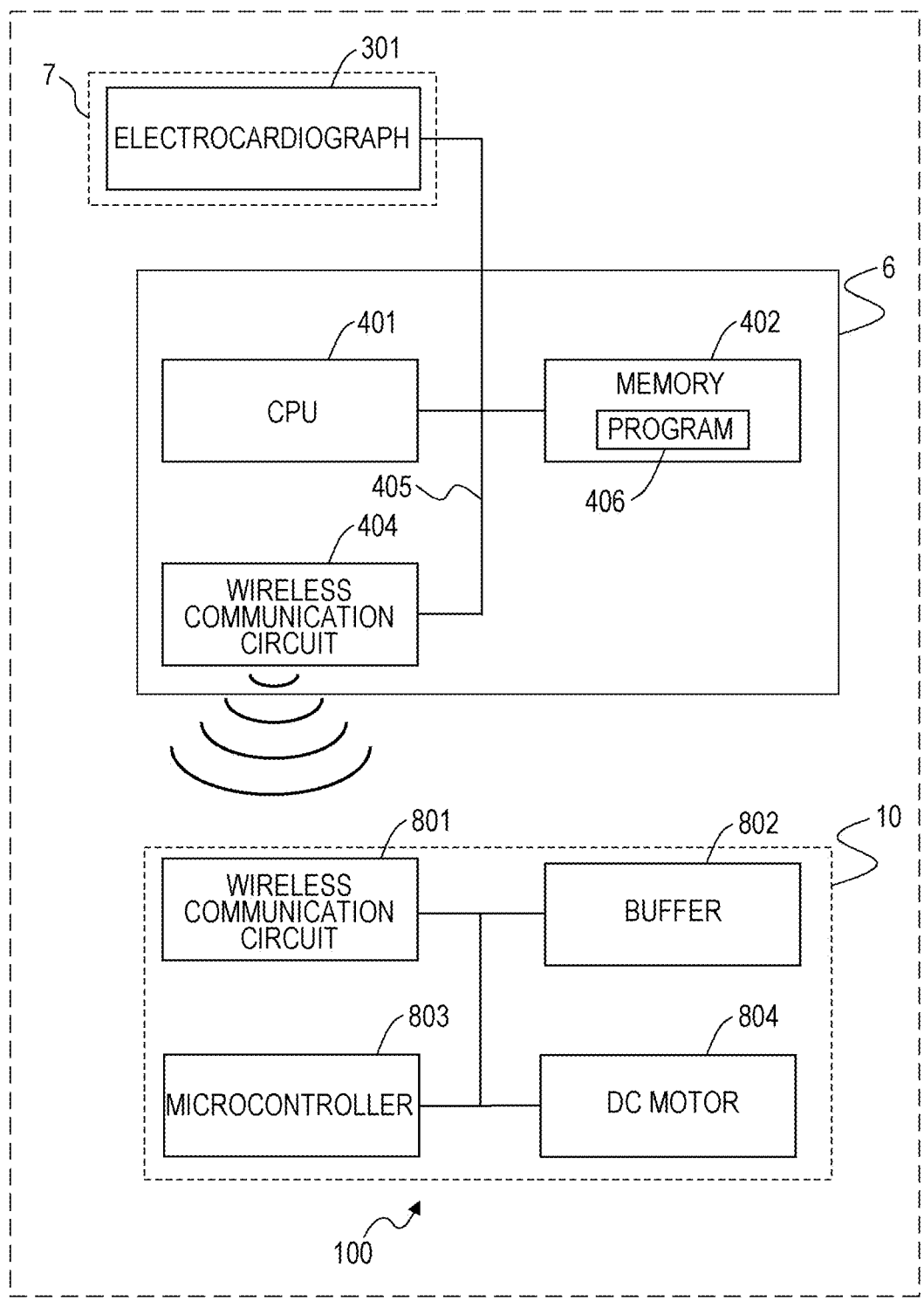
FIG. 3 illustrates an example of the hardware structure of the biofeedback system in the first embodiment.

FIG. 3 illustrates an example of the hardware structure of the biofeedback system 100. In FIG. 3, hardware components corresponding to the electrocardiographic sensor 7, controller 6, and feedbacker 10 are illustrated. Although a power supply is needed to operate the illustrated hardware components, it is not illustrated.

The electrocardiographic sensor 7, which is a known electrocardiograph, outputs a signal indicating an electrocardiogram of the user 1 in a wireless or wired manner.

The electrocardiographic measurer 3 and heart rate calculator 4 in the controller 6 are each composed of, for example, a signal processing circuit or processor (referred to below as the central processing unit (CPU)) 401, a memory 402, and a wireless communication circuit 404. These components, which are interconnected with a bus 405, can transmit and receive data among them.

The CPU 401 executes a computer program 406 stored in the memory 402 and controls the operations of the electrocardiographic measurer 3 and heart rate calculator 4. The computer program 406 is a set of commands that execute processing in the flowchart illustrated in FIG. 4. The CPU 401 also operates as the heart beat fluctuation calculator 11. A computer program corresponding to the processing, described above, by the heart beat fluctuation calculator 11 is also stored in the memory 402.

In addition, the CPU 401 calculates the average instantaneous heart beats. The term over which the average is calculated is shorter than half the period of the fluctuation cycle in the autonomic nerves at rest (that is, the feedback period). This average is repeatedly calculated in a period of, for example, half the feedback period. The CPU 401 creates a control signal by using the average heart rate of the user 1 at rest and information about the period of the fluctuation cycle in the autonomic nerves at rest (that is, the feedback period). The CPU 401 uses the created control signal to control the feedbacker 10. That is, if the average instantaneous heart rate, HRave, is smaller than the average heart rate at rest, HRconst, the CPU 401 creates a control command (that is, a control signal) to rotate a DC motor 804 in the normal direction. By contrast, if the HRave is larger than the HRconst, the CPU 401 creates a control command (that is, a control signal) to rotate the DC motor 804 in the reverse direction. Both control signals can include a signal that controls the rotational speed of the DC motor 804 and a term during which it rotates.

The wireless communication circuit 404 transmits and/or receives information by wireless according to a predetermined communication protocol. In this embodiment, the wireless communication circuit 404 transmits control signals created by the CPU 401. These control signals are received by a wireless communication circuit 801 included in the feedbacker 10, which will be described next.

The feedbacker 10 includes, for example, the wireless communication circuit 801, a buffer 802, a microcontroller 803, and the DC motor 804. The feedbacker 10 can be implemented as a radio-controlled model car that receives a control signal by wireless from, for example, the outside, and rotates the DC motor 804 in response to the control signal so as to drive the wheels and move the radio-controlled model car. The feedbacker 10 is formed by mounting the object driver 8 in the cabinet of the radio-controlled model car used as the object 2.

The wireless communication circuit 801 transmits and/or receives information by wireless according to a predetermined communication protocol. In this embodiment, the wireless communication circuit 801 receives control signals created by the CPU 401. The wireless communication circuit 801 sends a command indicated by a received control signal to the buffer 802. The buffer 802 stores the command.

The microcontroller 803 reads out commands stored in the buffer 802 in succession and executes these commands. If, for example, the microcontroller 803 executes a command to rotate the DC motor 804 in the normal direction, the microcontroller 803 makes the radio-controlled model car advance by controlling a current and/or a voltage to be supplied to the DC motor 804 so that the DC motor 804 rotates in the normal direction. Thus, the radio-controlled model car moves away from the user 1.

If the microcontroller 803 executes a command to rotate the DC motor 804 in the reverse direction, the microcontroller 803 backs up the radio-controlled model car by controlling a current and/or a voltage to be supplied to the DC motor 804 so that the DC motor 804 rotates in the reverse direction. Thus, the radio-controlled model car moves toward the user 1.

In addition to the rotational direction of the DC motor 804, its rotational speed and a term during which the DC motor 804 rotates are determined by control signals. Accordingly, it is possible to reciprocate the radio-controlled model car at a desired speed and in a desired period.

If the microcontroller 803 executes a command to stop the rotation of the DC motor 804, the microcontroller 803 shuts down or gradually reduces the current and/or voltage supplied to the DC motor 804. Thus, the radio-controlled model car stops moving.

An arrangement may be made so that when the DC motor 804 rotates in the normal direction, the radio-controlled model car moves toward the user 1 and that when DC motor 804 rotates in the reverse direction, the radio-controlled model car moves away from the user 1.

An object to move the radio-controlled model car toward the user 1 is to have the gazing user 1 cause convergence reflection as described above. By contrast, an object to move the radio-controlled model car away from the user 1 is to alleviate the convergence reflection caused in the user 1 as described above.

It can be said that the operation, implemented by the microcontroller 803, of the object 2 described above is originally controlled according to control signals, which have been created by the CPU 401. Therefore, it can be said that the CPU 401 induces the point of gaze of the user 1 from a near position to a far position and from a far position to a near position and synchronizes the breathing of the user 1 with the period of autonomic nerve fluctuations by using control signals to change the position of the object 2. However, it can be more directly said that the microcontroller 803 synchronizes the breathing of the user 1 with the period of autonomic nerve fluctuations and also synchronizes fluctuations in the diameter of the pupil of the user 1 with the period of autonomic nerve fluctuations by moving the object 2 in the period of autonomic nerve fluctuations according to control signals.

In the description with reference to FIG. 3, two semiconductor circuits, which are the CPU 401 and microcontroller 803, have been used, but this is just an example. Any circuit that can execute processing in response to a predetermined command can be used without being limited to the CPU 401 and microcontroller 803.

Next, the operation of the biofeedback system 100 will be described as the operation of the hardware illustrated in FIG. 3.

Figure 4:
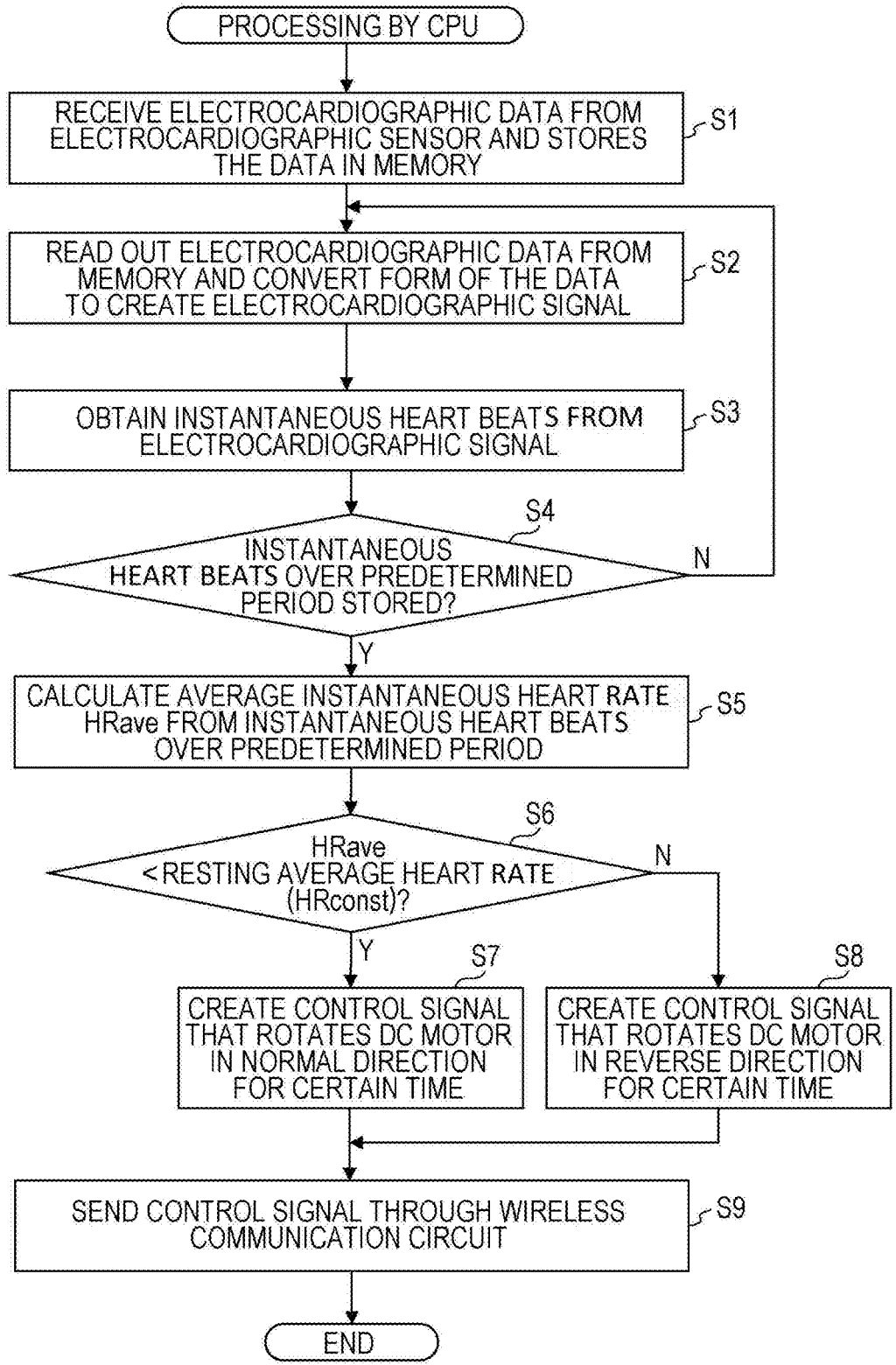
FIG. 4 is a flowchart indicating a procedure for processing executed by a CPU that is part of the electrocardiographic measurer and a heart rate calculator.

FIG. 4 is a flowchart indicating a procedure for processing executed by the CPU 401 that constitutes the electrocardiographic measurer 3 and heart rate calculator 4. It will be assumed that the average heart rate at rest has been obtained before processing in FIG. 4 starts.

In step S1, the CPU 401 receives electrocardiographic data from the electrocardiographic sensor 7 and stores the data in the memory 402.

In step S2, the CPU 401 reads out the electrocardiographic data from the memory 402 and converts the form of the data to create an electrocardiographic signal.

In step S3, the CPU 401 obtains instantaneous heart beats from the electrocardiographic signal. Details of this processing are as described above with reference FIGS. 2(a) to 2(e).

In step S4, the CPU 401 references the memory 402 and decides whether instantaneous heart beats over a predetermined term or longer is stored in the memory 402. If instantaneous heart beats over the predetermined term or longer is stored, processing proceeds to step S5. If not, processing returns to step S2. The predetermined term is, for example, a term that occupies half the period of the fluctuation cycle in the autonomic nerves at rest (that is, the feedback period), that is, a term that occupies part of the period.

In step S5, the CPU 401 calculates an average instantaneous hear rate, HRave, which is inverse of mean of average instantaneous heart beats over the predetermined term described above.

In step S6, the CPU 401 compares the HRave with an average heart rate at rest, HRconst. which is inverse of mean of instantaneous heart beats at rest. The HRconst has been obtained in advance. If the HRave is smaller than the HRconst, processing proceeds to step S7. If not, processing proceeds to step S8.

In step S7, the CPU 401 creates a control signal to rotate the DC motor 804 in the normal direction for a certain time. In step S8, the CPU 401 creates a control signal to rotate the DC motor 804 in the reverse direction for a certain time.

In step S9, the CPU 401 sends the created control signal to the wireless communication circuit 801 in the feedbacker 10 through the wireless communication circuit 404. Thus, the microcontroller 803 in the feedbacker 10 can rotate the DC motor 804 in the normal direction to make the object 2 advance or in the reverse direction to back up the object 2. The control signal to make the object 2 advance and the control signal to back up the object 2 do not necessarily have to be different signals. For example, a command to rotate the DC motor 804 in the normal direction only in the first half of the feedback period and to rotate the DC motor 804 in the reverse direction only in the latter half of the feedback period may be sent as a single control signal if the microcontroller 803 can interpret the control signal. As described above, processing to compare the HRave with the HRconst is performed at timings suitable to the feedback period (for example, at intervals of half the feedback period). Thus, a range within which the object 2 moves is adjusted, and the average instantaneous heart beats of the user 1 periodically changes within a range including the average heart beats. After the period in which the average instantaneous heart beats changes has stabilized, steps S1 to S6 may be omitted and steps S7 and S8 may be alternately repeated.

If, for example, direct memory access (DMA) technology is used, step S1 described above may not be executed by the CPU 401 itself.

The computer program 406 described above can be recorded in a compact disc-read-only memory (CD-ROM) or another recording medium and can be placed on the market as a product. Alternatively, the computer program 406 can be transmitted through the Internet or another electronic communication line.

Results in experiments conducted by the present inventor will be specifically described below.

A commercially available electrocardiograph can be used as the electrocardiographic sensor 7. However, the present inventor used an active electrode-type electrocardiograph that internally includes a pre-amplifier so that low noise can be measured. The electrocardiograph sends an electrocardiogram a to the CPU 401 in a wireless or wired manner. The CPU receives the digitized electrocardiogram.

The CPU 401 analyzed an interval between the peaks of each two adjacent R waves of the obtained electrocardiogram and converted the analysis result to instantaneous heart beats. The pseudo sampling frequency of the instantaneous heart beats was assumed to be 4 Hz or higher.

The CPU 401 analyzed fluctuations in the heart beats of the user 1 at rest from the obtained instantaneous heart beats. Specifically, the CPU 401 analyzed the peak frequency of the low-frequency component of the heart beat fluctuations taken as autonomic nerve fluctuations. The period of this low-frequency component is the period of the fluctuation cycle in the autonomic nerves of the user 1 at rest.

The present inventor moved the object 2 driven by the microcontroller 803 in the obtained period of the fluctuation cycle in the autonomic nerves of the user 1 at rest As described above, when the user 1 gazes at the object 2 and performs diaphragmatic breathing according to the position of the object 2, the user 1 is induced to cause a convergence reaction, so the pupil diameter cyclically changes. In response to this, fluctuations occur in synchronization with the diaphragmatic breathing.

The present inventor actually measured heart beat fluctuations by using the biofeedback system 100. Specifically, the present inventor first measured fluctuations at rest (Resting), after which the present inventor measured fluctuations in ordinary heat beat fluctuation biofeedback (HRV) that has been conventionally performed and in which a heart rate is fed back as a numeral and also measured fluctuations in biofeedback (HRV+PD) in this embodiment, in which heart beat fluctuations and pupil diameter fluctuations are synchronized with each other, in that order.

A feedback period was set to 11 seconds from a peak of the LF component of fluctuations in heart beats at rest.

Feedbacks were sent to the user 1 by the method described in this embodiment. That is, the object 2 was moved close to and away from the user 1 in a period of half of 11 seconds. Feedbacks concerning heart beats were sent according to the position of the object 2. In each biofeedback, fluctuations were measured for 150 seconds.

Figure 5A:
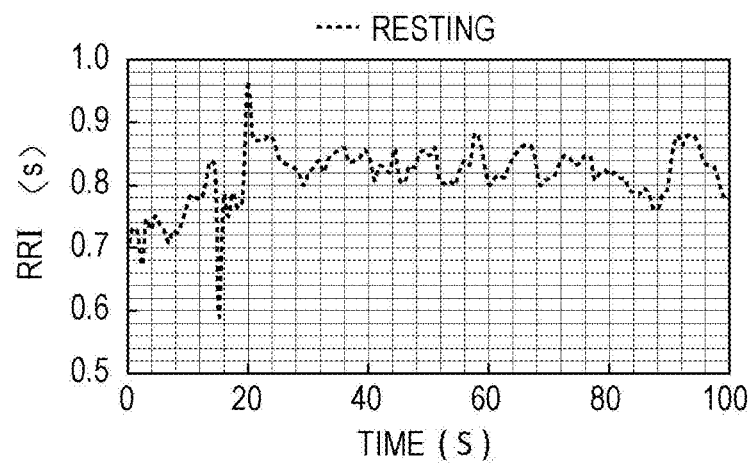
FIGS. 5A to 5C illustrate results of heart beat fluctuations in Resting, HRV, and HRV+PD.
Figure 5B:
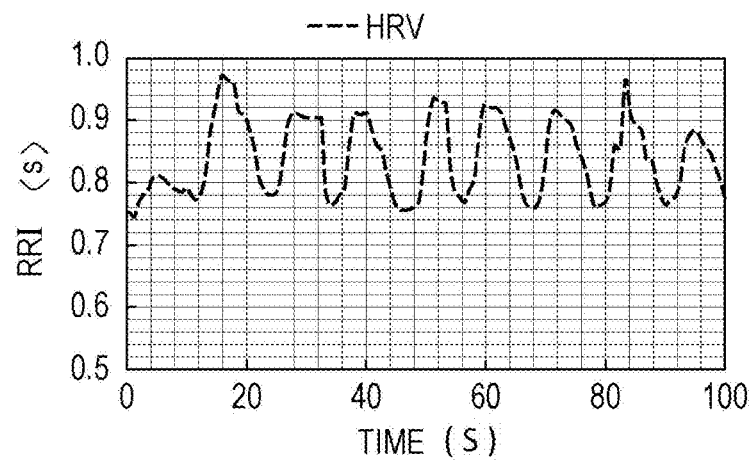
Figure 5C:
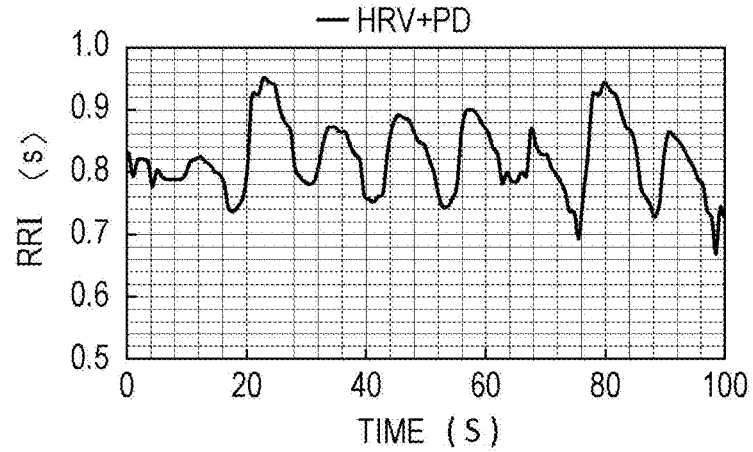

FIGS. 5A to 5C illustrate results of heart beat fluctuations in Resting, HRV, and HRV+PD. In HRV+PD in FIG. 5C, a calculation result obtained from the CPU 401, which operates as the heart beat fluctuation calculator 11, is illustrated.

Figure 6A:
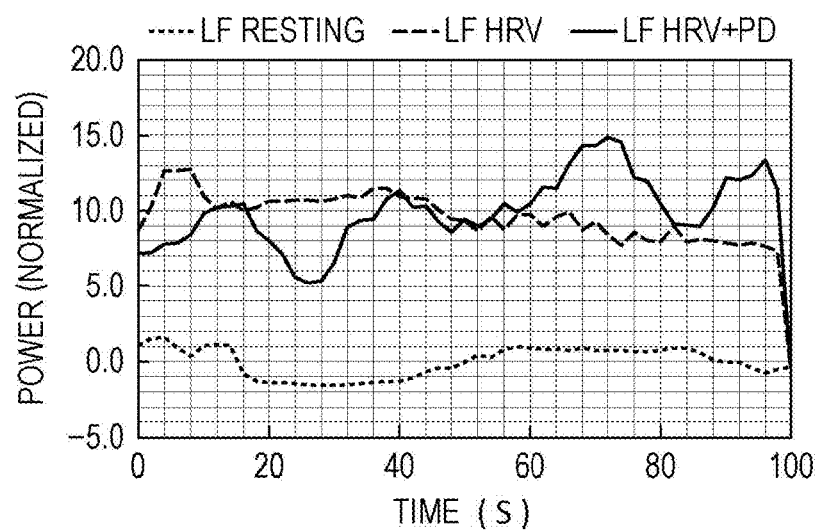
FIGS. 6A and 6B illustrate results of power spectra calculated with a width of 50 seconds at 2-second intervals.
Figure 6B:
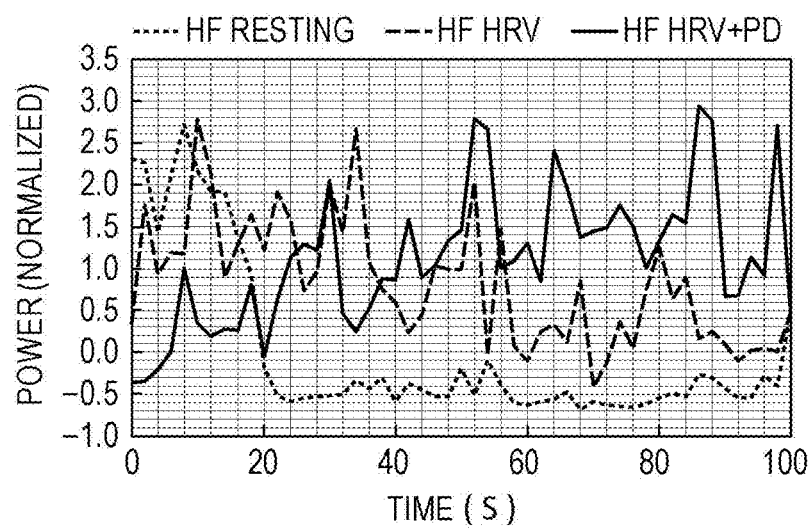

FIGS. 6A and 6B illustrate results of power spectra calculated with a width of 50 seconds at 2-second intervals. FIG. 6A indicates values obtained by integrating the LF component at 0.04 to 0.15 Hz. FIG. 6B indicates values obtained by integrating the high-frequency (HF) component at 0.15 to 0.50 Hz. However, values were standardized according to the results in Resting. The horizontal axis in FIGS. 6A to 6C indicates times at which a 50-second window started.

Results in analysis by the present inventor will be described below. It is found from the results of the LF component in FIG. 6A that the LF component is noticeably higher than at rest, indicating that biofeedback was satisfactorily implemented. From the results of the HF component in FIG. 6B, a difference is noted between conventional biofeedback and biofeedback in this embodiment in the HF region, which is not directly related to the feedback period. Particularly, after the elapse of 36 seconds, power integrated values in this embodiment are higher than power integrated values in conventional ordinary biofeedback (HRV), in which only heat beat fluctuation are used.

These results indicate that, in this embodiment, both the sympathetic nerve and the parasympathetic nerve can be efficiently activated. Biofeedback in this embodiment, in which heart beat fluctuations and pupil diameter fluctuations are synchronized with each other, is more efficient in autonomic nerve control than conventional heart rate variability biofeedback.

In summary, in processing described above, the user 1 is commanded to gaze at the object 2; since the user 1 gazes at the object 2, convergence reflection is periodically induced. That is, when the object 2 is moved toward the user 1, the pupil diameter is relatively reduced, and when the object 2 is moved away from the user 1, the pupil diameter is relatively enlarged. Therefore, in the method described above, the user 1 can periodically change the diameter of the pupil of the user 1 itself without being aware of having to change the pupil diameter.

Furthermore, since the user 1 is commanded to perform diaphragmatic breathing according to the position of the object 2, it is also possible to control heart beat fluctuations due to effects of heart rate variability biofeedback, as described in "Heart rate variability biofeedback" referred to above.

As a result, heart beat fluctuations and pupil diameter fluctuations are synchronized with each other. Since both heart beat fluctuations and pupil diameter fluctuations are subject to double domination as described above, periodic synchronous fluctuations in heart beats and the pupil diameter are expected to be fed back to the autonomic nerves in the brain more efficiently than in conventional heart rate variability biofeedback. In conclusion, the method in the present disclosure enables the balance of the autonomic nerves to be more reliably controlled than in the conventional examples.

The present inventor confirmed that heart rate variability biofeedback in the present disclosure is particularly effective when the degree of arousal of the user 1 is low.

Second Embodiment

FIG. 7 schematically illustrates the structure of a biofeedback system 200 in a second embodiment. In FIG. 7, the same constituent elements as in FIG. 1 will be assigned the same reference numerals and their descriptions will be omitted.

The second embodiment differs from the first embodiment in a method of determining fluctuations in the autonomic nerves of the user 1 at rest. In the first embodiment, autonomic nerve fluctuations have been determined from heart beat fluctuations. In the second embodiment, however, autonomic nerve fluctuations are determined from pupil diameter fluctuations.

In this embodiment, a pupil diameter image is obtained to obtain pupil diameter fluctuations and the pupil diameter in the image is identified. When images are obtained in succession, a period in which the pupil diameter changes can be obtained.

The biofeedback system 200 includes an imaging device 21, a controller 9, and the feedbacker 10. The controller 9 includes a pupil diameter calculator 22 and a pupil diameter fluctuation calculator 23, besides the structure in the controller 6 in the first embodiment.

The imaging device 21 photographs the pupil of the user 1 and obtains an image of the pupil. The obtained pupil image of the user 1 is sent to the pupil diameter calculator 22.

The pupil diameter calculator 22 calculates the pupil diameter from the pupil image. An algorithm to calculate the pupil diameter is the same as used in a generally available pupil diameter measuring apparatus. The algorithm will be described later.

The pupil diameter fluctuation calculator 23 operates before biofeedback is performed to obtain the period of the fluctuation cycle in the autonomic nerves of the user 1 (that is, feedback period). The imaging device 21 and pupil diameter calculator 22 operate before biofeedback is performed. The pupil diameter calculator 22 sends a signal that indicates a change in pupil diameter values to the pupil diameter fluctuation calculator 23. The pupil diameter fluctuation calculator 23 analyzes the frequency fluctuation of the signal, received from the pupil diameter calculator 22, that indicates a change in pupil diameter values. Specifically, the pupil diameter fluctuation calculator 23 calculates a power spectrum by a fast Fourier transform. In the fast Fourier transform, the present inventor used time-series information about pupil diameter values obtained over 50 seconds, as an example. Since the pupil diameter is subject to domination by the autonomic nerves as described above, pupil diameter fluctuations reflect autonomic nerve fluctuations. The pupil diameter fluctuation calculator 23 sends information about the obtained pupil diameter fluctuations to the object position controller 5.

Figure 8:
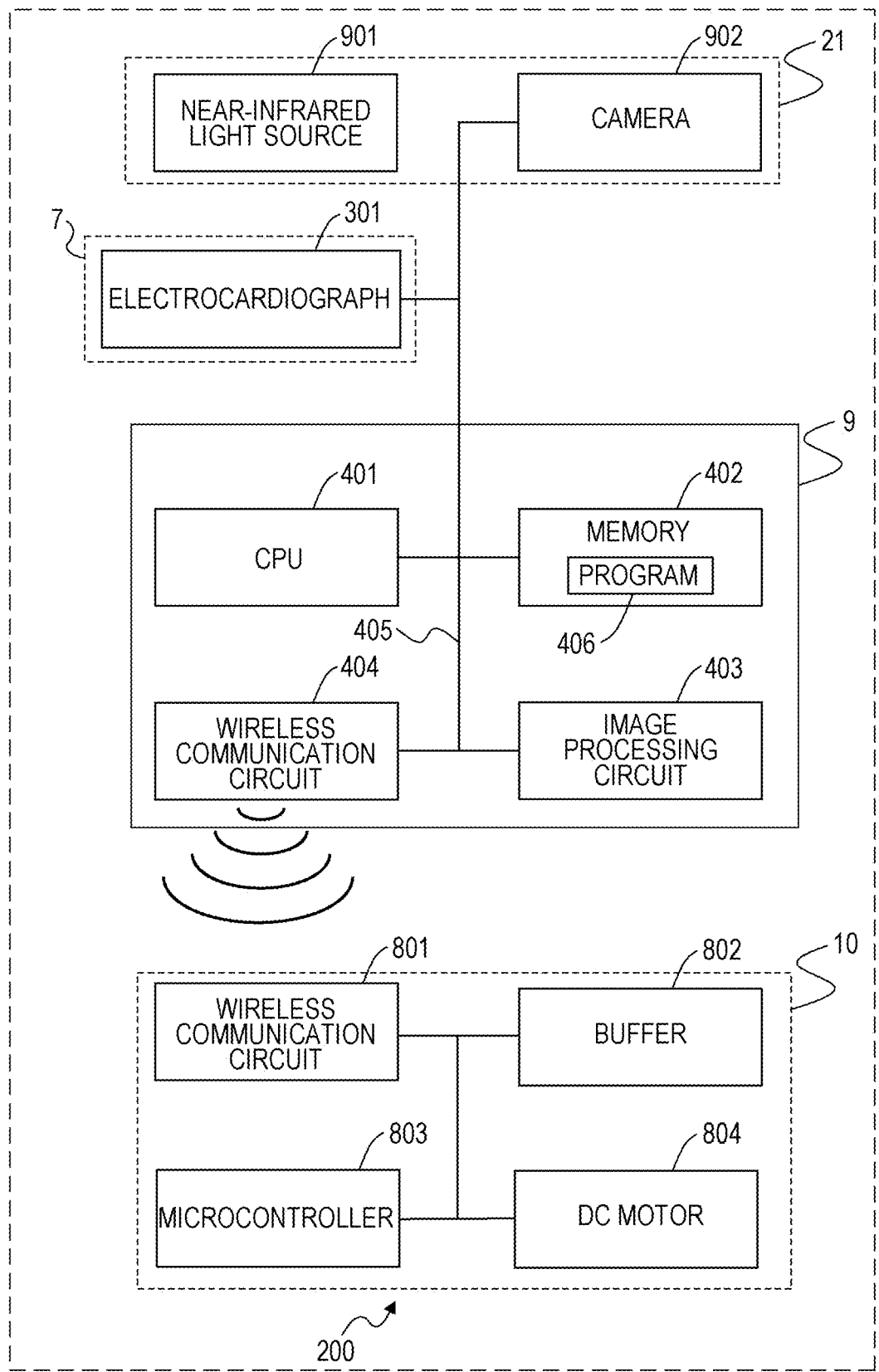
FIG. 8 illustrates an example of the hardware structure of the biofeedback system in the second embodiment.

FIG. 8 illustrates an example of the hardware structure of the biofeedback system 200.

The imaging device 21 includes, for example, a camera 902. The imaging device 21 may further include a near-infrared light source 901. The near-infrared light source 901 is a light emitting diode (LED) that emits light with a wavelength of, for example, 890 to 940 nm. The camera 902 has sensitivity to the wavelength of the near-infrared light source 901; the camera 902 can take a picture by receiving light with the wavelength. The camera 902 takes a moving picture at, for example, 30 to 300 Hz.

When an eye of the user 1 is photographed by using the above wavelength, even if the iris is dark brown in color and the pupil is black in color, the pupil can be clearly identified.

In FIG. 8, the near-infrared light source 901 has only a function that emits near-infrared light and is not connected to the camera 902. This is just an example. As another example, the near-infrared light source 901 may be mounted in the camera 902 and a signal line that can receive a control signal from the camera 902 may be provided so that the near-infrared light source 901 is turned on only in photography.

The pupil diameter calculator 22 is composed of, for example, the CPU 401, the memory 402, and an image processing circuit 403. These components, which are interconnected with the bus 405, can transmit and receive data among them. The CPU 401 may be operated as the image processing circuit 403 without the image processing circuit 403 being provided.

The pupil diameter fluctuation calculator 23 is composed of, for example, the CPU 401, memory 402, and wireless communication circuit 404.

The CPU 401 executes a computer program 407 stored in the memory 402 and executes processing corresponding to the pupil diameter calculator 22 and pupil diameter fluctuation calculator 23. The computer program 407 includes commands used to perform processing corresponding to the computer program 406 (see FIG. 3) and processing corresponding to the pupil diameter calculator 22 and pupil diameter fluctuation calculator 23.

The image processing circuit 403 is, for example, a graphic processor. In this embodiment, the image processing circuit 403 calculates the pupil diameter from a pupil image by performing processing described below. First, the image processing circuit 403 binarizes the obtained pupil image. An object of this binarization is to clarify the outline of the pupil.

The image processing circuit 403 applies an ellipse calculation algorithm to the binarized pupil image to identify an ellipse included in the image. The image processing circuit 403 retains the number of pixels corresponding to an ordinary pupil diameter in advance as a threshold. The threshold depends on the number of pixels in the camera 902, the distance between the user 1 and the camera 902, and other factors. A specific example will be described below.

The camera 902 used by the present inventor had 640 pixels vertically by 480 pixels horizontally. The present inventor adjusted the positions of the user 1 and camera 902 so that the whole of one eye of the user 1 is substantially included in the field of gaze of the camera 902.

Figure 9A:
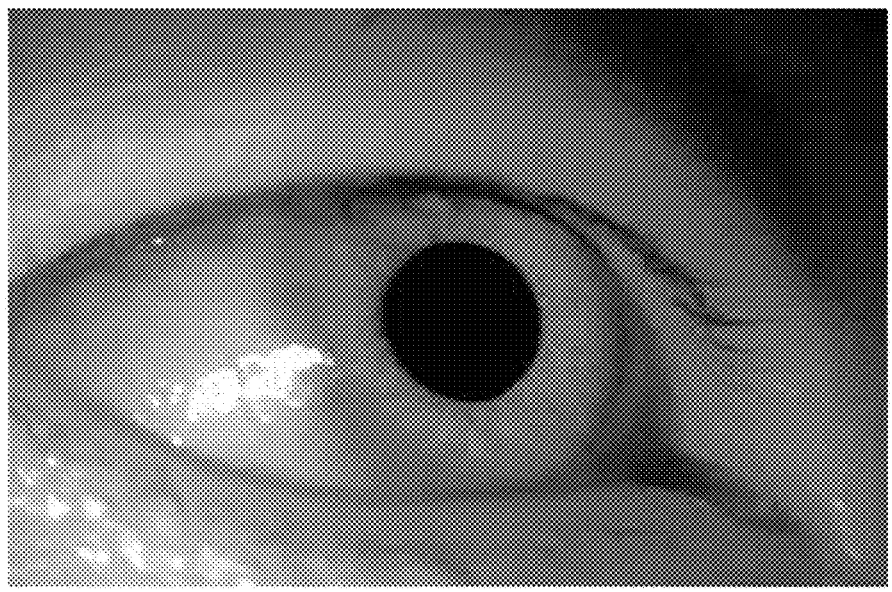
FIG. 9A illustrates an example of a user's eyeball image photographed with a camera.
Figure 9B:
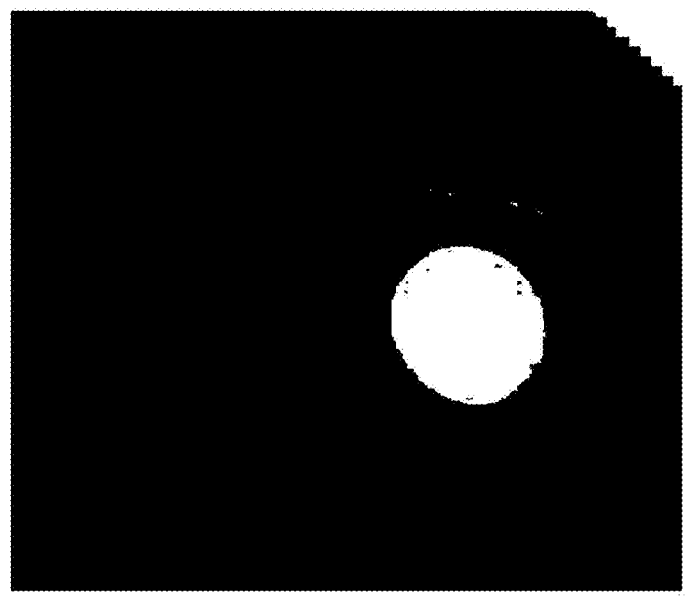
FIG. 9B illustrates part of an image binarized by an image processing circuit.

FIG. 9A illustrates an example of an image of an eyeball of the user 1, the image being captured with the camera 902. FIG. 9B illustrates part of an image binarized by the image processing circuit 403.

In this embodiment, a threshold was set for the brightness of each pixel to perform binarization. In this embodiment, since near-infrared light is emitted for photography, a threshold can be comparatively easily set. Specifically, as is clear from FIG. 9A, the pupil in the captured image is black in color, the iris spreading around the periphery of the pupil is light gray in color, and the outer side of the iris (that is, the tail side of the eye) is white in color. It suffices to set, as a threshold, a value by which each brightness value can be classified as a brightness value corresponding to a black portion of the pupil or another brightness value.

The image processing circuit 403 makes a decision for each pixel in the captured image as to whether the pixel is larger or equal to or smaller than the threshold set for the pixel. If a pixel has a brightness value equal to or smaller than a certain brightness value, the image processing circuit 403 converts the pixel to a white pixel. If the pixel has a brightness value larger than the certain brightness value, the image processing circuit 403 converts the pixel to a black pixel. An image obtained in this way is the image in FIG. 9B. The black pupil in FIG. 9A is represented as a white region in FIG. 9B, and almost all other regions are represented in black. Processing described above is just an example. The pupil may be converted to a black region.

Next, the image processing circuit 403 detects, as a pupil region, a region that is included in the white region in the binarized pupil image (see FIG. 9B) and has a size within a predetermined range. In the experiments carried out by the present inventor, the longer axis of the pupil image was about 20 pixels long in the case of a test subject having a short longer axis and about 150 pixels long in the case of a test subject having a long longer axis; typically (or on the average), the longer axis of the pupil image was about 60 pixels long. The image processing circuit 403 detects, as the pupil region, a white region including a straight line that is, for example, 20 to 150 pixels long. When processing as described above is included, even if an ellipse area is included in a region other than the pupil, it is possible to prevent the region from being decided as the pupil by mistake. In the processing described above, not only an ellipse but also a perfect circle can be detected as a pupil region candidate.

The image processing circuit 403 obtains the length of the longer axis by using, for example, a parallelogram inscribed to the ellipse. The image processing circuit 403 links the midpoints of each two opposing sides of the parallelogram inscribed to the ellipse to obtain two straight lines and identifies the intersection of the two straight lines as the center of the ellipse. The image processing circuit 403 then identifies, as the pupil diameter, the maximum length of line segments, each of which is formed by linking two points on the outline of the ellipse so as to pass through the center of the ellipse.

If near-infrared light emitted from the near-infrared light source 901 is reflected on the cornea at a position near to the pupil, part of the pupil image has high brightness due to reflected light, in which case part of the elliptical region may be lost. The portion having high brightness is called an outlier. The presence of an outliner disables an elliptical region from being detected. However, various technologies to remove an outlier have been developed. Therefore, the removal of an outliner will not be described in this description. It is desirable to remove an outliner before the elliptical region and pupil diameter are detected as described above.

Since the pupil diameter is identified while photography is in progress, the operating frequency when the image processing circuit 403 calculates the pupil diameter is higher than the frequency at which the camera 902 captures an image.

The CPU 401 receives the pupil diameter data identified by the image processing circuit 403. Since pupil diameter images are constantly obtained, pupil diameter data is also accumulated. The CPU 401 performs processing described above to calculate the period of pupil diameter fluctuations from the accumulated pupil diameter data.

The wireless communication circuit 404 sends information about the period of pupil diameter fluctuations to the microcontroller 803, which functions as the object driver 8, through the wireless communication circuit 801. Therefore, the object driver 8 can obtain the period of pupil diameter fluctuations as the period of autonomic nerve fluctuations prior to a biofeedback operation.

After the acquisition of the period of autonomic nerve fluctuations, the biofeedback system 200 operates like the biofeedback system 100 in the first embodiment.

As described above, it becomes possible to maximize or minimize the pupil diameter fluctuations due to autonomic nerves fluctuations and to control the pupil diameter according to the state of the user 1. As a result, desired autonomic nerve control is preferably achieved.

Third Embodiment

Figure 10:
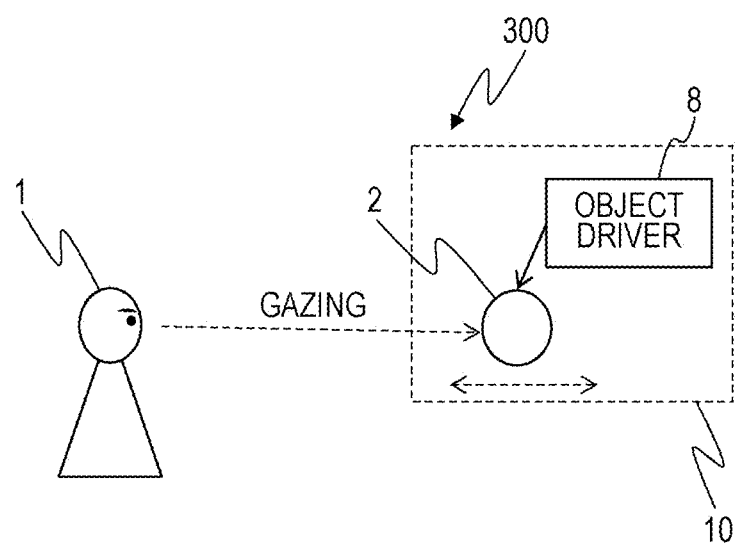
FIG. 10 schematically illustrates the structure of a biofeedback system in a third embodiment.
Figure 11:
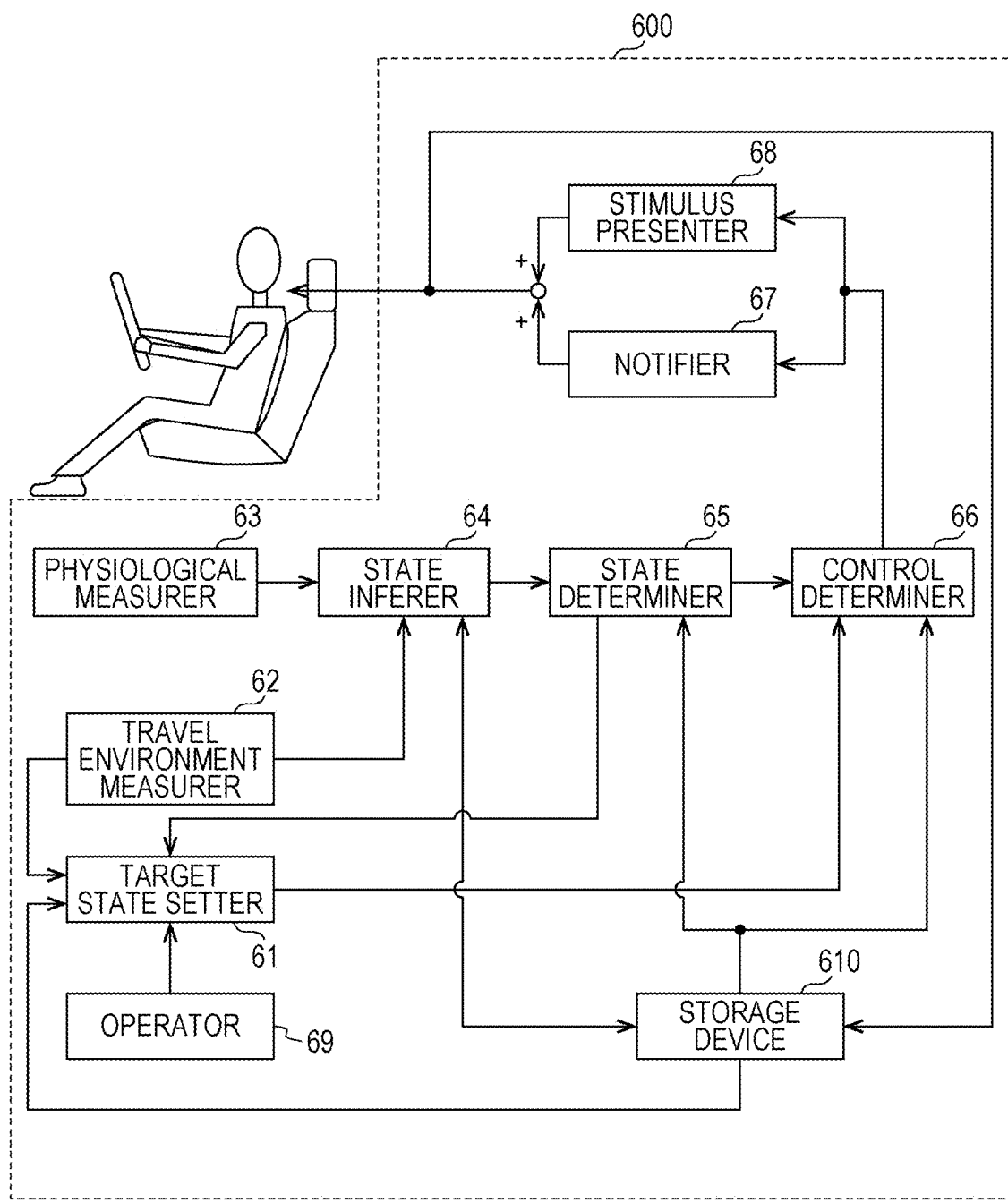
FIG. 11 illustrates a conventional biofeedback apparatus described in Japanese Unexamined Patent Application Publication No. 2008-125802.
Figure 12:
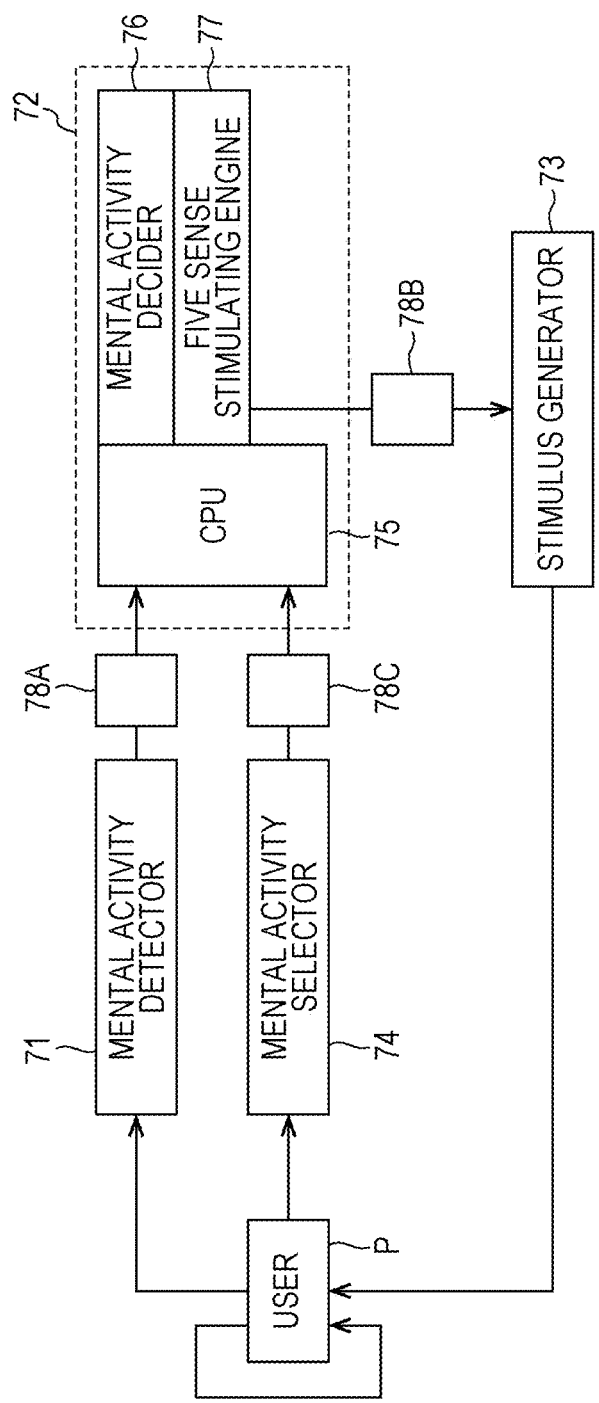
FIG. 12 illustrates a conventional biofeedback apparatus described in Japanese Unexamined Patent Application Publication No. 2001-252265.

FIG. 10 schematically illustrates the structure of a biofeedback system 300 in this embodiment.

Unlike the first and second embodiments, the biofeedback system 300 in this embodiment uses only the period of autonomic nerve fluctuations of the user 1 at rest, the period having been obtained in advance, to have the object 2 continue to move fore and aft in the period of the fluctuation cycle. In this case, the physiological signal of the user 1 does not need to be obtained, so, naturally, the period does not need to be adjusted by using the physiological signal.

That is, the biofeedback system 300 controls the movement period of the object 2 regardless of the current physiological state of the user 1 so that the pupil diameter is reduced in the period of autonomic nerve fluctuations and that the user 1 is induced to breathe in synchronization with the movement period of the object 2 to cause heart beat fluctuations to synchronize with autonomic nerve fluctuations. Information about the period of the fluctuation cycle in the autonomic nerves at rest may be obtained from fluctuations in heart beats at rest as in the first embodiment or by a method, as in the second embodiment, in which fluctuations in the pupil diameter at rest are used. Alternatively, the average of the period of the fluctuation cycle in the pupil diameter at rest and the period of the fluctuation cycle in heart beats at rest may be used as the period of autonomic nerve fluctuations.

Hardware in the feedbacker 10, which is included in the biofeedback system 300 and has the object 2 and object driver 8, is the same as, for example, hardware in the feedbacker 10 in the biofeedback system 100 in the first embodiment, except that unlike the first embodiment, the object driver 8 does not need to obtain instantaneous heart beats and an average instantaneous heart beats from an electrocardiogram, nor does it need to compare the HRave which is inverse of mean of instantaneous heart beats with the HRconst which is inverse of mean of heat beats at rest. Since there is no need to use information about the average instantaneous heart beats, the object driver 8 does not perform processing related to information about the either pupil diameter values or heart beat values. The object driver 8 only needs to move the object 2 from a near position to a far position and a far position to a near position in the period of autonomic nerve fluctuations and to command the user 1 to inhale while the object 2 moves away from the user 1 and to exhale slowly in another term. This enables the period of the autonomic nerves to be controlled.

The differences described above appear as differences in, for example, the operation of the microcontroller 803 and information stored in the buffer 802, the microcontroller 803 and buffer 802 being illustrated in FIG. 3. The buffer 802 stores, for example, information about the period of the fluctuation cycle in the autonomic nerves of the user 1 at rest, the period having been measured in advance. The microcontroller 803 induces the point of gaze of the user 1 from a near position to a far position and from a far position to a near position by moving the object 2 on the basis of only information, stored in the buffer 802, about the period of autonomic nerve fluctuations. The microcontroller 803 may issue a command to the user 1 from a display (not illustrated) or a speaker (not illustrated), if necessary. A command is issued in the form of an image or a voice. The user 1 is prompted to inhale while the object 2 moves away from the user 1 and to exhale slowly in another term.

In the structure in this embodiment, if the period of autonomic nerve fluctuations can be obtained as a minimum, a facility used to obtain a physiological signal from the user 1 does not need to be introduced, so the biofeedback system 300 can be very easily introduced.

The user 1 only needs to gaze at the moving object 2 and breathe according to the position of the moving object 2. Therefore, biofeedback can be achieved very easily.

This completes the description of the exemplary embodiments of the present disclosure.

Variation

In the above embodiments, examples in which the electrocardiographic sensor 7 is used have been described. However, a pulse wave sensor that measures pulse waves may be used instead of the electrocardiographic sensor 7. A pulse wave has a waveform representing a change in volume caused by a blood flow into a certain portion in body tissues, the change being captured from a body surface. A pulse wave reflects a vasomotion reaction. It is thought that when the motion of a peripheral blood vessel rather than the motion of the heart itself is measured, information having a meaning similar to an RR interval on an electrocardiogram is indirectly obtained. Therefore, a pulse wave can be processed as in processing to obtain an electrocardiogram.

In the above embodiments, a biofeedback method of moving an actual object (a radio-controlled model car, for example) and a system that moves it have been described. However, this is just an example. The object referred to in this description is not limited to a tangible object, but may be an intangible object such as a point of light emitted from a laser and is projected onto a floor or wall.

Furthermore, the present inventor confirmed that even when a virtual object on a three-dimensional display is used instead of an existing object such as a radio-controlled model car, similar effects are obtained. Specifically, a three-dimensional image of an object is displayed on a screen as an object, after which the point of gaze of the user 1 is adjusted to the object by having the user 1 gaze at the object. Then, the size of the object displayed on the screen is changed. If, for example, the size of the object displayed on the screen is changed so as to be reduced, the same effect is obtained as when the point of gaze of the user 1 is virtually moved from a near position to a far position. Conversely, if the size of the object displayed on the screen is changed so as to be increased, the same effect is obtained as when the point of gaze of the user 1 is virtually moved from a far position to a near position.

Furthermore, at least two lamps, for each of which a time at which the lamp is turned on can be individually set, are attached at positions apart from the user 1 by different distances, instead of a self-propelled object. The user 1 is commanded to gaze at a turned-on lamp. The lamp to be turned on is changed from the lamp at a position close to the user 1 to the lamp at a position far from the user 1. Thus, the same effect is obtained as when an object is moved from a position close to the user 1 to a position far from the user 1.

Conversely, when the lamp to be turned on is changed from the lamp at a position far from the user 1 to the lamp at a position close to the user 1, the same effect is obtained as when an object is moved from a position far from the user 1 to a position close to the user 1. The present inventor confirmed that it is possible to induce the user 1 to cause convergence reflection by these methods as well. Times at which to turn on the lamps can be easily controlled by using a PC, a microcontroller, or the like. Thus, the same effects as described above can be obtained.

The intensity of light incident on the eye of the user 1 may be changed in the period of autonomic nerve fluctuations. For example, the user 1 is commanded to gaze at a light, and the brightness of the light may be changed (or the light may be turned on and off) in the period of autonomic nerve fluctuations.

A command to the user 1 in the first to third embodiments and the variation may be made by using a commanding apparatus. The commanding apparatus includes, for example, a computer, a memory, and a display and/or speaker. The memory stores data of an image and/or voice presented to the user 1. The computer reads out the data from the memory. The computer may control the display so that an image is displayed on the display and/or may control the speaker so that a voice is output, according to the read-out data. Alternatively, a commander may give a command to the user 1.

In addition, the diameter of the pupil of the user 1 may be forcibly changed in synchronization with the period of autonomic nerve fluctuations, without using a command. For example, the brightness of a light in the room in which the user 1 is present may be changed (or the light may be turned on and off) in the period of autonomic nerve fluctuations. Furthermore, the user 1 may be made to wear a head-mounted display, and the brightness of the head-mounted display may be changed (or the head-mounted display may be turned on and off) in the period of autonomic nerve fluctuations. In these cases, the diameter of the pupil of the user 1 can be forcibly changed in synchronization with the period of autonomic nerve fluctuations, without using a command.

Furthermore, the breathing of the user 1 may be forcibly changed in synchronization with the period of autonomic nerve fluctuations, without using a command. For example, a belt equipped with an airbag may be worn around the waist of the user 1, after which air may be supplied to or may be released from the airbag in the period of autonomic nerve fluctuations. Thus, the waist of the user 1 is pressed in the period of autonomic nerve fluctuations.

The pupil diameter fluctuation biofeedback method and biofeedback system in the present disclosure are effective in the detection and alleviation of stress and also effective as a method and system that are used to simply manage and alleviate stress in a personal daily life. The pupil diameter fluctuation biofeedback method and biofeedback system can also be applied to, for example, management and alleviation of the daily stress of employees at companies and members at organizations. With the method of using autonomic nerve fluctuations and the system using these fluctuations in the present disclosure, the balance of the autonomic nerves can be maintained and adjusted more simply, more easily, and more practically than in the conventional methods.

What is claimed is:

1. A method comprising:
   (a) obtaining, by a processor, information about a period of a fluctuation cycle in an autonomic nerve of a user;
   (b) inducing the user to breathe in synchronization with the period of the fluctuation cycle in the autonomic nerve according to the obtained information; and
   (c) synchronizing a fluctuation in a diameter of a pupil of the user with the period of the fluctuation cycle in the autonomic nerve according to the obtained information, wherein
   the period of the fluctuation cycle in the autonomic nerve is (i) a period of a fluctuation cycle in a heart beats of the user, or (ii) a period calculated from the period of the fluctuation cycle in the diameter of the pupil and the period of the fluctuation cycle in the heart beats, and
   in (c), the fluctuation of the diameter of the pupil of the user is synchronized with the period of the fluctuation cycle in the autonomic nerve by repeating, in the period of the fluctuation cycle in the autonomic nerve, a process that includes inducing a point of gaze of the user to move in a direction away from the user and inducing the point of gaze of the user to move in a direction to approach the user.

2. The method according to claim 1, wherein the period of the fluctuation cycle in the autonomic nerve is a period corresponding to a peak frequency in a predetermined frequency band included in a fluctuation in a heart beats of the user.

3. The method according to claim 2, wherein the predetermined frequency band is from 0.04 to 0.15 Hz.

4. The method according to claim 3, wherein, in (c), if a heart rate of the user is higher than an average heart rate of the user, the point of gaze of the user is induced to move in a direction to approach the user.

5. The method according to claim 1, wherein, in (b), when the point of gaze of the user is induced to move in a direction away from the user in (c), the user is induced to inhale.

6. The method according to claim 1, wherein, in (c), the repeating of the process includes
   (c1) adjusting the point of gaze to an object by having the user gaze at the object, and
   (c2) alternately repeating, after (c1), motion of the object in a direction away from the user and motion of the object in a direction to approach the user.

7. The method according to claim 1, wherein, in (c), the repeating of the process includes
   (c1) adjusting the point of gaze to a position illuminated by light by having the user gaze at the position illuminated by the light, and
   (c2) alternately repeating, after (c1), movement of the position illuminated by the light in a direction away from the user and movement of the position illuminated by the light in a direction to approach the user.

8. The method according to claim 2, wherein information about the period of the fluctuation cycle in the heart beats is obtained from an electrocardiogram obtained in a measurement.

9. The method according to claim 2, wherein information about the period of the fluctuation cycle in the heart beats is obtained by measuring a pulse wave.

10. A system comprising:
   a storage device that holds information about a period of a fluctuation cycle in an autonomic nerve of a user; and
   a processor that creates a control signal according to the information held in the storage device, the control signal being used to move an object, the processor synchronizing breathing of the user with the period of the fluctuation cycle in the autonomic nerve by moving the object in the period of the fluctuation cycle in the autonomic nerve in response to the control signal, the processor synchronizing a fluctuation in a diameter of a pupil of the user with the period of the fluctuation cycle in the autonomic nerve, wherein the fluctuation of the diameter of the pupil of the user is synchronized with the period of the fluctuation cycle in the autonomic nerve by repeating, in the period of the fluctuation cycle in the autonomic nerve, a process that includes inducing a point of gaze of the user to move in a direction away from the user and inducing the point of gaze of the user to move in a direction to approach the user.

11. A system comprising:

a storage device that holds information about a period of a fluctuation cycle in an autonomic nerve of a user; and a controller that repeats a process that includes inducing a point of gaze of the user to move in a direction away from the user and inducing the point of gaze of the user to move in a direction to approach the user in the period of the fluctuation cycle in the autonomic nerve by moving an object in response to a control signal based on the information held in the storage device, the controller synchronizing breathing of the user with the period of the fluctuation cycle in the autonomic nerve, wherein a fluctuation of a diameter of a pupil of the user is synchronized with the period of the fluctuation cycle in the autonomic nerve by repeating, in the period of the fluctuation cycle in the autonomic nerve, the process that includes inducing the point of gaze of the user to move in the direction away from the user and inducing the point of gaze of the user to move in the direction to approach the user.

* * * * *